United States Patent [19]

Rabinowitz

[11] Patent Number: 4,535,761

[45] Date of Patent: Aug. 20, 1985

[54] GUM MASSAGER

[75] Inventor: Lewis Rabinowitz, Glendale, Ariz.

[73] Assignee: Arnell Inc., Glendale, Ariz.

[21] Appl. No.: 391,530

[22] Filed: Jun. 24, 1982

[51] Int. Cl.³ .............................................. A61H 7/00
[52] U.S. Cl. ................................................ 128/62 A
[58] Field of Search ....................... 128/62 A; 132/89; 15/110; D4/24; D28/64

[56] References Cited

U.S. PATENT DOCUMENTS

| | | | |
|---|---|---|---|
| 1,996,205 | 4/1935 | Jackson | 128/62 A |
| 2,042,239 | 5/1936 | Planding | 15/110 |
| 2,141,969 | 12/1938 | Benz | 128/62 A |
| 2,527,857 | 10/1950 | Strachan | 128/62 A |
| 2,600,136 | 6/1952 | Staunt | 128/62 A |
| 2,888,008 | 5/1959 | Rosenthal | 128/62 A |
| 3,050,072 | 8/1962 | Diener | 128/62 A |
| 3,129,449 | 4/1964 | Cyzer | 128/62 A |
| 3,368,553 | 2/1968 | Kirby | 128/62 A |
| 4,296,518 | 10/1981 | Furrier et al. | 15/110 |
| 4,335,472 | 6/1982 | Rappleyea | 2/421 |

Primary Examiner—Richard J. Apley
Assistant Examiner—David J. Brown
Attorney, Agent, or Firm—Herbert E. Haynes, Jr.

[57] ABSTRACT

Apparatus (10) for massaging gums has a handle portion (12, 12') arranged for manipulating the apparatus (10) in order to impart an undulating motion to a substantially rigid massaging portion (14) arranged for insertion between adjacent teeth of a user of the apparatus. A coupling (16) connected to the handle portion (12, 12') and the massaging portion (16) articulate same to one another and permits the aforementioned undulating motion which causes a vibrating effect against the gum. The coupling preferably is in the form of a universal joint (42) in order to enhance the aforementioned undulating motion.

6 Claims, 17 Drawing Figures

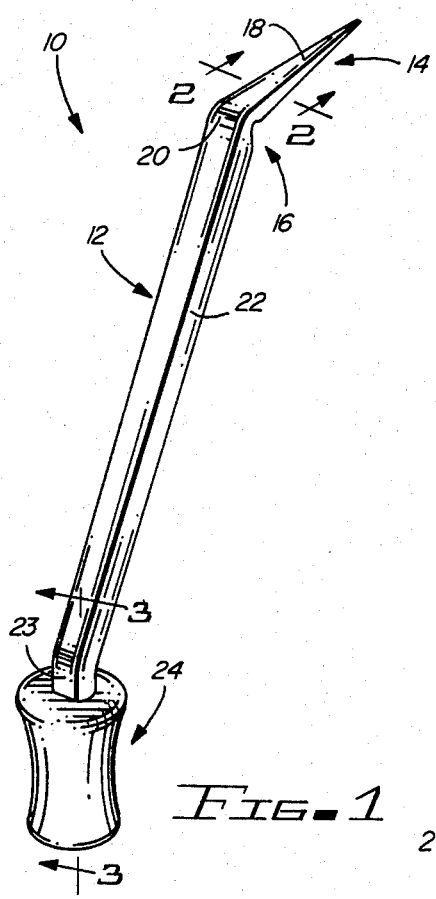
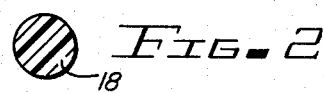
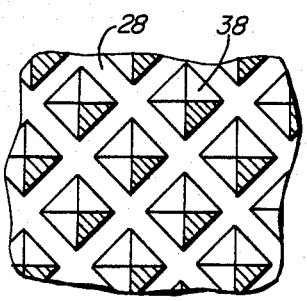
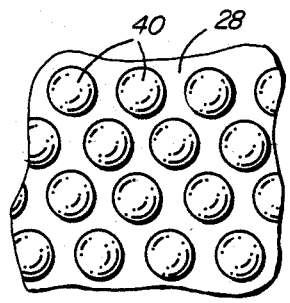
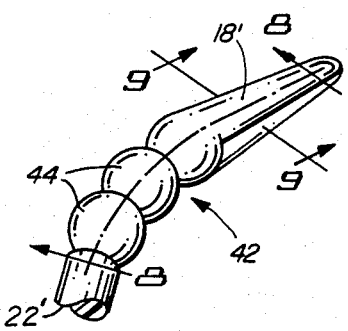
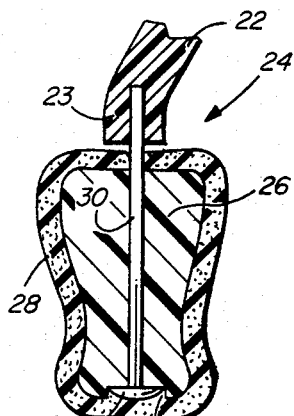
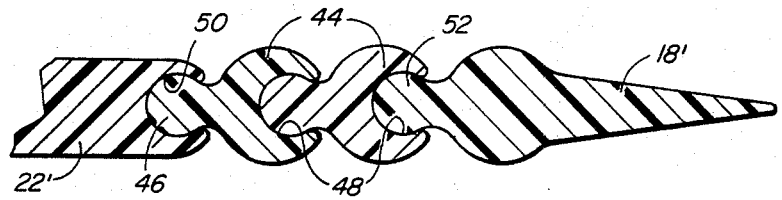
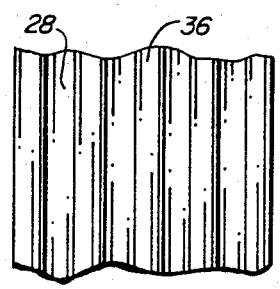
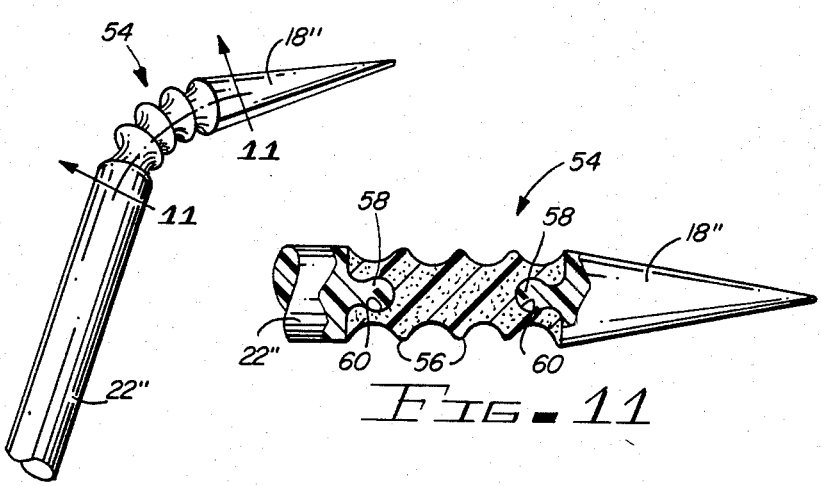

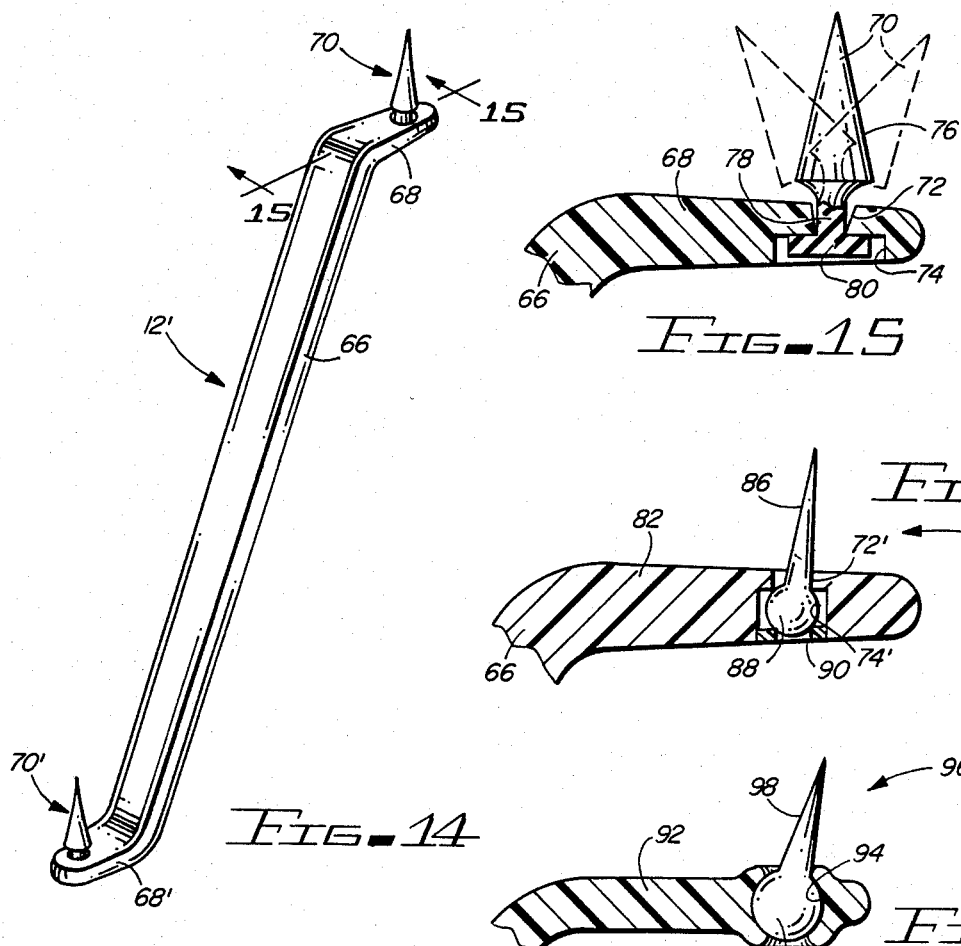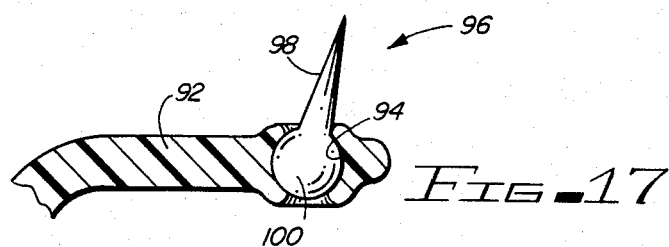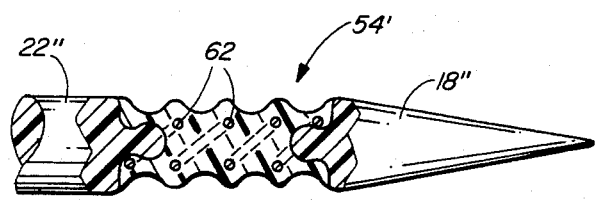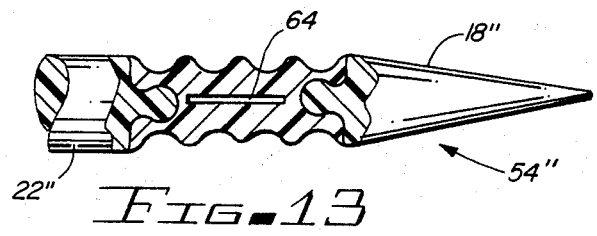

GUM MASSAGER

BACKGROUND OF THE INVENTION

1. Field of the Invention

This invention relates generally to dental appliances, and more particularly to apparatus for massaging areas of a user's gums located between the user's teeth.

2. Description of the Prior Art

The desirability of massaging ones gums has long been known. U.S. Pat. No. 1,086,936, issued Feb. 10, 1914, to M. Pounder, et al., discloses a dental massage implement having a generally conoidal massaging head rotatably mounted on one end of a manipulating handle. This known massaging head is generally formed from a resilient material such as a soft rubber, and advantageously is provided with longitudinally extending ribs arranged for producing a desired vibratory effect. A basic disadvantage with this prior device is that a conoidal configuration does not properly fit the outer surfaces of gums being massaged.

Another known gum massager device is disclosed in U.S. Pat. No. 2,091,511, issued on Aug. 31, 1937, to B. London. This known device employs a pair of massager tips fabricated from rubber and disposed at respective free ends of similar spring arms projecting from a common handle. The massager tips each are in the configuration of a conventional door knob, and the like, and once again do not readily conform to the surface of gums being massaged.

U.S. Pat. Nos. 1,533,528, issued Apr. 14, 1925, to J. A. Weaver, and 2,074,735, issued Mar. 23, 1937, to J. Puttcamp, disclose devices intended to be used for massaging ones back and ones face, respectively. The latter is of a conoidal configuration as discussed above, while the former employs a symmetrical, grooved roller, the hyperboloid configuration of this roller, while more suitable for gum massaging than the aforementioned conoidal configurations, still is not optimumly suited for gum massaging applications.

In addition to massaging the outer and inner surfaces of ones gums, it is desirable to massage the areas of gums disposed between ones teeth. Although it is known to provide flexible toothpicks, as set forth in U.S. Pat. No. 516,409, issued Mar. 13, 1894, to C. C. Southwell, such appliances are suitable only for their intended use, that of cleaning between adjacent teeth, and do not provide the requisite vibratory action desired for gum massaging operations. Further, U.S. Pat. No. 710,498, issued Oct. 7, 1902, to D. McClain, discloses a toothpick having a rigid point set at a right angle to the shank thereof, which arrangement is also capable only of cleaning between adjacent teeth and not massaging the associated gum area. The same can be said for the toothpick disclosed in U.S. Pat. No. 1,654,230, issued Dec. 27, 1927, to H. Zimmerman, and to the rigid hook forming the rear end of a handle of a toothbrush as disclosed in U.S. Pat. No. 1,784,986, issued Dec. 16, 1930, to S. Eisenberg.

U.S. Pat. No. 4,205,664, issued June 3, 1980, to M. O. Baccialon, discloses a tooth and gum massaging implement having a pair of rigid massaging elements of different configurations extending from opposed ends of a longitudinally extending handle portion. Once again, however, the massaging elements are rigidly attached to the associated handle, making it impossible to obtain a desired vibratory action against gums being massaged.

U.S. Pat. No. 3,985,147, issued Oct. 12, 1976, to C. M. Ricketts, et al., discloses a dental implement for removing stains from teeth in which a pick and hole are rigidly disposed on one end of a longitudinally extending handle, at the other longitudinal end of which is provided a disc. As with the devices described above, this appliance is intended only for cleaning teeth, and is not capable of achieving a vibratory action desired for massaging gums.

SUMMARY OF THE INVENTION

It is an object of the present invention to provide a gum massaging appliance capable of providing an undulating or vibratory motion when massaging gum areas located between adjacent teeth.

It is another object of the present invention to provide a gum massaging appliance capable of massaging gum areas between adjacent teeth in all parts of a user's mouth.

Still another object of the present invention is to provide a gum massaging appliance, or apparatus, capable of conformingly engaging inner and outer side surfaces of ones gums for effectively and efficiently massaging same.

These and other objects are achieved according to the present invention by providing a gum massaging apparatus comprising a handle part arranged for manipulating the apparatus and having attached thereto a substantially rigid massaging part insertable between teeth of a user of the apparatus. The massaging part is articulated to the handle part by a coupling which permits undulating motion of the massaging part relative to the handle part.

The massaging part preferably includes a tapered massaging element constructed from a soft yet rigid material selected for preventing damage to a user's gums. In one preferred embodiment of the present invention, the handle part and massaging part are formed as a single piece, and the coupling includes an integral hinge connecting the handle part to the massaging part.

In another preferred embodiment of the present invention, the coupling includes an universal joint removably connected to the handle part and to the massaging part for articulating same to one another. This universal joint can comprise at least one ball-and-socket member attached to the handle part and massaging part, or a flexible piece of material provided with a connector associated with the piece of material and with the handle part and massaging part for attaching same together. In order to improve resiliency, or springiness, of the flexible piece of material, a spring element may be embedded therein.

The handle part preferably includes a straight portion and an offset portion, with the massaging part further comprising a gum massaging device rotatably mounted in spaced relation to the tapered element and arrangable for massaging inner and outer surfaces of gums being massaged. This gum massaging device includes a rigid core of an unsymmetrical hyperboloid configuration and covered with a resilient material directly engagable with gums being massaged and which can have a textured surface of various designs to facilitate the massaging action.

A further embodiment of the present invention has the handle part including a straight portion and an offset portion, but with the massaging part comprising a massaging element of generally conical configuration and arranged mounted on the offset portion so as to extend therefrom. The handle part may include a pair of such offset portions extending in spaced relation from the straight portion so as to form a symmetrical arrangement with each of the offset portions being provided with a respective massaging element, each like the one massaging element and extending cordirectionally of each other.

The foregoing and other objects of this invention as well as the invention itself, may be more fully understood when read in conjunction with the following drawings.

BRIEF DESCRIPTION OF THE DRAWINGS

FIG. 1 is a generally diagrammatic, perspective view showing a first embodiment of gum massaging apparatus according to the present invention.

FIG. 2 is an enlarged, sectional view taken generally along the line 2—2 of FIG. 1.

FIG. 3 is an enlarged, fragmentary, sectional view taken generally along the line 3—3 of FIG. 1.

FIG. 4 is an enlarged, fragmentary, elevational view showing one possible surface texture for a roller as seen in FIG. 3.

FIGS. 5 and 6 are enlarged, fragmentary, elevational views similar to FIG. 4, but showing modified surface textures for a roller as seen in FIG. 3.

FIG. 7 is a fragmentary, perspective view showing a second embodiment of a gum massaging apparatus according to the present invention.

FIG. 8 is a enlarged, fragmentary, sectional view taken generally along the line 8—8 of FIG. 7.

FIG. 9 is an enlarged, sectional view taken generally along the line 9—9 of FIG. 7.

FIG. 10 is a fragmentary, perspective view showing yet another embodiment of gum massaging apparatus according to the present invention.

FIG. 11 is an enlarged, fragmentary, generally sectional view taken along the line 11—11 of FIG. 10.

FIGS. 12 and 13 are views similar to that seen in FIG. 11, but showing modified arrangements of resilient couplings.

FIG. 14 is a generally diagrammatic, perspective view showing still another embodiment of the present invention.

FIG. 15 is an enlarged, fragmentary, sectional view taken generally along the line 15—15 of FIG. 14.

FIGS. 16 and 17 are views similar to FIG. 15, but showing modified arrangements of mounting a massaging element in accordance with the present invention.

DESCRIPTION OF THE PREFERRED EMBODIMENTS

Referring now more particularly to FIGS. 1 and 2 of the drawings, an apparatus 10 according to the present invention for massaging gums comprises a handle part 12 arranged for manipulating apparatus 10 and having articulated thereto a substantially rigid massaging part 14 insertable between teeth (not shown) of a user of apparatus 10 for massaging the associated gum area of same. Connection of massaging part 14 to handle part 12 is carried out in the embodiment of FIGS. 1 and 2 by use of a coupling 16 permitting part 14 to undulate, or wiggle, relative to part 12.

Massaging part 14 includes a tapered massaging element 18 constructed from a soft yet rigid material selected for preventing damage to a user's gums. In the embodiment of the invention under discussion, parts 12 and 14 are formed as a single piece, with coupling 16 including an integral hinge 20 constructed in a conventional manner to permit the aforementioned undulating movement of part 14 relative to part 12. The latter includes a rigid, gripping portion 22 terminating at a longitudinal end spaced from hinge 20 in an offset, or angularly inclined, portion 23 on which is rotatably mounted a gum massaging device 24 arrangable for massaging the inner and outer side surfaces (not shown) of a user's gums. In this manner, the selective use of massaging part 14 and massaging device 24 permits complete massaging of ones gums in an efficient and effective manner.

Referring more specifically to FIG. 3, massaging device 24 includes a rigid core 26, which may be constructed from a suitable synthetic resin, wood, metal, and the like, having an unsymmetrical hyperboloid configuration with a larger head disposed adjacent portion 22 of part 12 and having a covering 28 of a suitable resilient material, such as a natural or synthetic rubber, for cushioned engagement with a user's gums. Core 26 has extending longitudinally thereto a bore arranged for rotatably journaling core 26 on a shaft 30 terminating at a downward portion thereof in a head 32 preferably arrangable in a recess 34 provided in the lower end of core 26 so as to eliminate a protuberance or bulge in that area. Shaft 30 can be fittingly inserted into a suitable hole provided in offset portion 23 of handle part 12 so as to provide a rigid support for journaling core 26.

As can be seen from FIGS. 4 through 6, covering 28 can be smooth as indicated in FIG. 3, or can be provided with various surface texturing to enhance the massaging action thereof. Thus, FIG. 4 illustrates one possible surface texture in the form of longitudinal ribs 36 extending from the upper enlarged head to the lower one of device 24, in order to form a corrugated surface, while FIG. 5 shows a patterned surface generally in the form of knurling 38. FIG. 6 illustrates a surface having a pattern of hemispherical protuberances 40. It will be appreciated that various other surface textures, patterns, and designs can be used as desired and appropriate.

Referring now to FIGS. 7 through 9, a second embodiment of the present invention is illustrated wherein a coupling between a handle part gripping portion 22' and a tapered massaging element 18' is formed by a universal joint 42 removably connected to portion 22' and element 18' for articulating same to one another for universal, undulating movement. In the specific embodiment illustrated in FIGS. 7 through 9, universal joint 42 is formed by at least one, and preferably the illustrated plurality of ball-and-socket members 44 attached to handle portion 22' and massaging element 18'. The members 44 each comprise a ball 46 and a spaced socket 48, with a ball 46 engagable in a socket 48 of an associated member 44 and with a socket 50 provided in, for example, handle portion 22'. Massaging element 18 may have, in addition to an enlarged portion adjacent the base end thereof, a ball 52 of similar size to a ball 46 so as to movably engage in a socket 48 of an adjacent member 44.

As can be best seen from FIG. 9, element 18' has an alternative cross section to that of element 18 (FIG. 2) in that it is ellipsoid. While the material used to construct the embodiment illustrated in FIGS. 7 through 9 may vary, it is contemplated that it will be constructed from a suitable synthetic resin having some springiness thereto in order to form snap fits between balls 46, 52 and sockets 48, 50.

FIGS. 10 and 11 of the drawings disclose yet another embodiment of the present invention wherein a universal joint coupling comprises a flexible piece 54 of a suitable resilient material, such as a natural or synthetic rubber, preferably having the illustrated ribs 56 to enhance bending movement in a known manner. Connection of piece 54 to associated handle portion 22" and a massaging element 18" can be accomplished in any suitable manner, such as by the illustrated balls 58 and cooperating sockets 60.

FIGS. 12 and 13 disclose additional embodiments similar to that seen in FIGS. 10 and 11, but additionally being provided with a resilient element embedded in the flexible piece of material forming the coupling between the handle portion 22" and a massaging element 18". More specifically, FIG. 12 shows the use of a conventional coiled spring 62 embedded within a piece 54', while FIG. 13 discloses the use of a length of spring or resilient wire 64 embedded in the flexible piece 54". As can be appreciated, any suitable configuration for a resilient element can be employed, although it is preferable that the resulting spring action have universal movement.

Referring now more particularly to FIG. 14 of the drawings, an embodiment of the present invention is illustrated wherein a handle part 12' includes a straight portion 66 and at least one and preferably the illustrated pair of offset portions 68 and 68' terminating longitudinally spaced ends of portion 66. Each of the portions 68 and 68' is provided with a respective massaging element 70 and 70' preferably arranged so as to extend codirectionally as illustrated in order to provide a pair of different angles facilitating massaging of gum areas in all parts of ones mouth. As seen in FIG. 15, each of the massaging elements 70, 70' is mounted on an associated one of the offset portions 68, 68', as by an outwardly flaired or diverging bore 72 having a countersunk area 74 in the lower or narrowest area thereof. Since FIG. 15 illustrates specific offset portion 68, only that portion will be referred to in the following discussion, with it being understood that offset 68' and its associated massaging element 70' can be attached to one another in an identical manner.

Massaging element 70 includes a generally tapered portion 76 constructed from a soft yet fairly rigid material, such as a natural or synthetic rubber, and similar to materials used for massaging tips commonly provided on handles of toothbrushes. Thus, conical portion 76 will be fairly rigid near the base thereof, but will tend to become flexible toward its apex. Extending downwardly from the base area of portion 76 is a shank 78 of greatly reduced diameter relative to the base of portion 76, with shank 78 terminating in a head 80 arrangable in the countersunk area 74 so as to retain element 70 on offset portion 68. As can be appreciated, and as illustrated by broken lines in FIG. 15, the shank 78 will permit flexing of portion 76 relative to its holding portion 68. Accordingly, a desired universal, undulating motion is achieved in a simple yet effective manner.

Referring to FIGS. 16 and 17, additional examples of mounting a massaging element on an offset portion of a handle part 12' are illustrated. More specifically, FIG. 16 illustrates an arrangement wherein an offset portion 82 movably mounts a massaging element 84 having a generally conical portion 86 merging at the base end thereof to a sphere 88 retained in a countersunk area 74' as by the illustrated retainer 90 so as to permit portion 86 movement within the bore 72'. Similarly, FIG. 17 provides an offset portion 92 in which a generally spherical cavity 94 is integrally formed so as to receive a massaging element 96 having a generally conical portion 98 extending from a sphere 100 universally, movably arranged within cavity 94. Insertion of sphere 100 within cavity 94 may be achieved in any suitable manner, such as by constructing offset portion 92 of a material suitably flexible to permit snap insertion of sphere 100 into the cavity.

As can be readily understood from the above description and from the drawings, gum massaging apparatus according to the present invention permits one to massage gums, including the areas between teeth, in a simple yet efficient manner simply by inserting the tapered massaging element between adjacent teeth and permitting same to undulate relative to the gripping handle part. The undulation sets off vibrations which facilitate the massaging action. Apparatus according to the present invention can be constructed in a simple manner, with the specific materials being a matter of choice from among conventionally used materials such as rubbers, vinyls, and the like.

While the principles of the invention have now been made clear in illustrated embodiments, there will be immediately obvious to those skilled in the art, many modifications of structure, arrangements, proportions, the elements, materials, and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claim is:

1. Apparatus for massaging gums, comprising in combination:
    (a) handle means for manipulation of the apparatus;
    (b) a substantially rigid massaging means arranged for insertion between the teeth of a user of the apparatus; and
    (c) a universal joint coupling means interconnecting said handle means and said massaging means so that said massaging means normally extends perpendicularly from said handle means, said universal joint coupling means being cooperatively formed by a bore means provided transversely in said handle means and an axially extending shank and an enlarged head provided on said massaging means, said shank extending through the bore means of said handle means and being of slightly reduced diameter in relation to the bore means of said handle means to allow a free changing of the angular relationship between said massaging means and said handle means and to allow a swivel-like movement to be imparted to said massaging means upon insertion of said massaging means between the teeth of the user and upon manipulation of said handle means.

2. Apparatus as defined in claim 1 wherein said massaging means further includes a tapered massaging element constructed from a soft yet rigid material selected for preventing damage to a user's gums.

3. Apparatus as defined in claim 1 wherein said handle means includes a straight portion and an offset portion, said massaging means being mounted on the offset portion by said universal joint coupling means.

4. Apparatus for massaging gums, comprising in combination:

(a) handle means for manipulation of the apparatus, said handle means having opposed surfaces;
(b) a massaging means for insertion between the teeth of a user of the apparatus, said massaging means including,
   I. a body of generally conical configuration,
   II. a flexible shank extending axially from the base of said conical body and being of reduced diameter in comparison to the base of said conical body,
   III. an enlarged head on the extending end of said shank; and
(c) a universal joint coupling means interconnecting said handle means and said massaging means so that said massaging means normally extends substantially perpendicularly from one of the surfaces of said handle means, said coupling means including, said handle means having a bore formed transversely therethrough so as to provide a portion which divergingly opens onto the surface of said handle means which faces the base of said conical boby and having a countersunk area in the opposite surface of said handle means, said enlarged head being disposed in said countersunk area of said bore with said flexible shank extending through said diverging portion of said bore, said flexible shank having a diameter which is slightly smaller than the smallest diameter of said diverging portion of said bore to alow a free changing of the angular relationship between said massaging means and said handle means and to allow a swivel-like movement of said massaging means upon insertion of said massaging means between the teeth of the user and manipulation of said handle means.

5. Apparatus as claimed in claim 4 wherein said conical body, said shank and said enlarged head of said massaging means are integrally formed.

6. Apparatus as defined in claim 5 wherein said massaging means is formed of a soft yet rigid material selected for preventing damage to a user's gums.

* * * * *